United States Patent [19]
Slepian et al.

[11] Patent Number: 6,071,956
[45] Date of Patent: Jun. 6, 2000

[54] TREATMENT OF TISSUES TO REDUCE SUBSEQUENT RESPONSE TO INJURY

[75] Inventors: Marvin J. Slepian; Stephen P. Massia, both of Tucson, Ariz.

[73] Assignee: Endoluminal Therapeutics, Inc., Tucson, Ark.

[21] Appl. No.: 09/158,725

[22] Filed: Sep. 23, 1998

Related U.S. Application Data

[62] Division of application No. 08/321,128, Oct. 11, 1994, Pat. No. 5,914,345.

[51] Int. Cl.[7] .......................... A01N 55/06; A61K 31/305
[52] U.S. Cl. .......................... 514/496; 604/101; 604/102; 604/95; 604/96; 604/97; 604/98; 604/99; 604/163; 604/191; 604/194; 604/195
[58] Field of Search .............................. 514/496; 604/101, 604/102, 103, 95, 96, 97, 98, 99; 606/191, 194, 195

[56] References Cited

U.S. PATENT DOCUMENTS

| | | |
|---|---|---|
| 550,238 | 11/1895 | Allen, Jr. . |
| 3,173,418 | 3/1965 | Baran . |
| 4,224,929 | 9/1980 | Furihata . |
| 4,417,570 | 11/1983 | Finnieston . |
| 4,423,725 | 1/1984 | Baran et al. . |
| 4,445,892 | 5/1984 | Hussein et al. . |
| 4,536,407 | 8/1985 | Shay . |
| 4,601,986 | 7/1986 | Wegner et al. . |
| 4,636,195 | 1/1987 | Wolinsky . |
| 4,693,720 | 9/1987 | Scharnberg et al. . |
| 4,797,359 | 1/1989 | Finkelstein . |
| 5,007,916 | 4/1991 | Linskey et al. . |
| 5,071,962 | 12/1991 | Morrison et al. . |

(List continued on next page.)

FOREIGN PATENT DOCUMENTS

| | | |
|---|---|---|
| 2 678 949 | 1/1993 | France . |
| WO 95/09659 | 4/1995 | WIPO . |

OTHER PUBLICATIONS

Elia, Guiliano, et al., "Regulation Of Heat Shock Protein Synthesis By Quercetin In Human erythroleukemia Cells", *Biochem. Journal* 300(1):201–209 (1994) Abstract.

Gonzalez, Manuel F., et al., "Heat shock proteins as markers of neural injury," *Molecular Brain Res.* 6:93–100 (1989).

Gromkowski, Stanislaw, et al., "Elevated temperature regulates tumor necrosis factor–mediated immune killing," *Eur. J. Immunol.* 19:1709–1714 (1989).

Hightower, Lawrence E. and Peter T. Guidon, Jr., "Selective Release From Cultured Mammalian Cells of Heat–Shock (Stress) Proteins That Resemble Glia–Axon Transfer Proteins," *J. of Cell. Physiol.* 138:257–266 (1989).

(List continued on next page.)

*Primary Examiner*—Shelley A. Dodson
*Assistant Examiner*—Michael A. Williamson
*Attorney, Agent, or Firm*—Arnall Golden & Gregory, LLP

[57] ABSTRACT

An exogenous stimulus is applied to tissues or cells which are at risk in a subsequent surgical procedure or other intervention which induces a response by the cells that minimizes reaction to the subsequent procedure. Stimuli can be chemical, physiological or physical. Examples include those stimuli known to induce expression of stress response proteins or heat shock proteins, especially heat shock protein 70 (hsp 70) and hsp 90, for example, exposure to heat or dilute hydrogen peroxide, or direct administration of exogenous heat shock proteins, or those stimuli which act to inhibit or reduce heat shock protein expression, for example, treatment with flavonoids. An amount effective to modulate levels of stress response proteins or reduce the endogenous response is administered, based on in vitro assays which are used to determine levels of heat shock proteins or which are experimentally determined to reduce cell proliferation, thrombus formation, and matrix deposition following subsequent exposure to a procedure. Procedures can be surgery, angioplasty, or abrasion. The method and compositions are also useful in mediating some disease processes, where the process involves undesirable migration.

13 Claims, 2 Drawing Sheets

U.S. PATENT DOCUMENTS

| | | |
|---|---|---|
| 5,087,244 | 2/1992 | Wolinskey . |
| 5,092,841 | 3/1992 | Spears . |
| 5,137,805 | 8/1992 | Kingston et al. . |
| 5,213,580 | 5/1993 | Slepian et al. . |
| 5,279,565 | 1/1994 | Klein et al. . |
| 5,295,962 | 3/1994 | Crocker et al. . |
| 5,306,249 | 4/1994 | Michel . |
| 5,306,250 | 4/1994 | March et al. . |
| 5,328,471 | 7/1994 | Slepian . |
| 5,445,146 | 8/1995 | Belinger . |
| 5,519,035 | 5/1996 | Maiese et al. . |
| 5,527,864 | 6/1996 | Suggs et al. . |

OTHER PUBLICATIONS

Hill–West, et al., "Prevention of Postoperative Adhesions in the Rat by In Situ Photopolymerization of Bioresorbable Hydrogel Barriers," *Obst. Gyne.* 83:59 (1994).

Hosokawa, Nobuko, et al., "Flavonoids Inhibit the Expression of Heat Shock Proteins," *Cell Structure and Function Jap. Soc. Cell Biol.* 393–401 (1990) Abstract.

Hosokawa, Nobuko, et al., "Inhibition Of The Activation Of Heat Shock Factor In Vivo And In Vitro By Flavonids", *Mol. Cell Biol.*, 12(8):3490–3498 (1992) Abstract.

Jaattela, Marja, et al., "Major heat shock protein hsp70 protects tumor cells from tumor necrosis factor cytotoxicity," *The EMBO Journal* 11:3507–3512 (1992).

Johnson, A. Daniel and Michael Tyler, "Exogenous Hsp70 Becomes Cell Associated, But Not Internalized by Stressed Arterial Smooth Muscle Cells," *In Vitro Cell Dev. Biol.* 29A:807–812 (1993).

Kang, et al., "Requirement for hsp70 in the mitochondrial matrix for translocation and folding of precursor proteins," *Nature* 348, 137–143 (Nov. 1990).

Kantengwa, Salome, et al., "Flavonoids, But Not Protein Synthesis During Erythrophagocytosis", *Biochem. Biophys. Res. Commun.*, 180(1):308–314 (1991) Abstract.

Alexandrov, Vladimir Ya., "Functional Aspects of Cell Response to Heat Shock," *Int. Rev. of Cytology* 148:171–227 (1994).

Amrani, Mohamed, et al., "Induction of Heat–Shock Proteins Enhances Myocardial and Endothelial Functional Recovery After Prolonged Cardioplegic Arrest," *Ann. Thorac. Surg.* 57:157–160 (1994).

Baker and Schatz, "Mitochondrial proteins essential for viability mediate protein import into yeast mitochondria" *Nature* 349, 205–208 (Jan. 1991).

Black, S.C. and B. R. Luchesi, "Heat Shock Proteins and the Ischemic Heart," *Circulation* 83(3):1048–51 (1993).

Ciocca, Daniel R., et al., "Biological and Clinical Implications of Heat Shock Protein 27000 (Hsp27): a Review," *J. of Nat. Cancer Inst.* 85:1558–1570 (1993).

Courgeon, Anne–Marie, et al., "Effect of Hydrogen Peroxide on Cytoskeletal Proteins of Drosophila Cells: Comparison with Heat Shock and Other Stresses," *Exp. Cell Res.* 204:30–37 (1993).

Cress, Anne E., et al., "Alteration of Cellular Adhesion by Heat Shock," *Exp. Cell Res.* 190:40–46 (1990).

Currie, R.W., et al., "Heat–Shock Response and Limitation of Tissue Necrosis During Occlusion/Reperfusion in Rabbit Hearts," *Circulation* 87(3):965–971 (1993).

Deshaies, R.J., et al., "A subfamily of stress proteins facilitates translocation of secretory and mitochondrial precursor polypeptides," *Nature* 332, 800–805 (1988).

Duncan, Roger F. and John W. B. Hershey, "Protein Synthesis and Protein Phosphorylation during Heat Stress, Recovery and Adaptation," *J. Cell Biol.* 109:1467–1481 (1989).

Kaufmann, "Heat shock proteins and the immune response" *Immunol. Today* 11:129–137 (1990).

Ketis, Nika, V., et al., "Extracellular Matrix Components Affect the Pattern of Protein Synthesis of Endothelial Cells Responding to Hyperthermia," *In Vitro Cell Dev. Biol.* 29A:768–772 (1993).

Ketis, Nika, V., et al., "Effects of Heat Shock on the Expression of Thrombospondin by Endothelial Cells in Culture," *J. of Cell Biol.* 106:893–904 (1988).

Ketis, Nika, V., et al., "Effects of Hyperthermia on Cell Survival and Patterns of Protein Synthesis in Endothelial Cells from Different Origins," *Cancer Res.* 48:2101–2106 (1988).

Laszlo, Andrei, "The Thermoresistant State: Protection from Initial Damage or Better Repair?" *Exp. Cell Res.* 202:519–531 (1992).

Levinson, Warren, et al., "Transition Series Metals and Sulfhydryl Reagents Induce the Synthesis of Four Proteins in Eukaryotic Cells," *Biochim. Biophys. Acta* 606:170–180 (1980).

Lindquist and Craig, "The heat–shock proteins" *Annu. Rev. Genet.* 22:631–677 (1988).

Lindquist, "The heat–shock response" *Ann. Rev. Biochem.* 55:1151–1191 (1986).

Luscinskas, Francis W. and Jack Lawler, "Integrins as dynamic regulators of vascular function," *The FASEB Journal* 8:929–938 (1994).

Majda, John A., et al., "Heat Shock–Induced Shedding of Cell Surface Integrins in A549 Human Lung Tumor Cells in Culture," *Exp. Cell Res.* 210:46–51 (1994).

Morimoto "Heat shock: the role of transient inducible responses in cell damage, transformation, and differentiation" *Cancer Cells* 3:295–301 (1991).

Murakami, Yuko, et al., "Induction of Hsp 72/73 by Herbimycin A, an Inhibitor of Transformation by Tyrosine Kinase Oncogenes," *Exp. Cell Res.* 195:338–344 (1991).

Nadeau, Kari, et al., "Hsp90 Chaperonins Possess ATPase Activity and Bind Heat Shock Transcription Factors and Peptidyl Prolyl Isomerases," *J. of Biol. Chem.* 268:1479–1487 (1993).

Nover, "HSFs and HSPs—a stressful program on transcription factors and chaperones." Stress Proteins, and the Heat Shock Response, sponsored by Cold Spring Harbor Laboratory (Cold Spring Harbor, NY USA Apr. 29–May 2, 1991) *New Biol.* 3:855–859 (1991).

Nover and Scherf Heat shock protein, in *Heat Shock Response* (CRC Press, 1991) pp. 41–127.

Pechan, Paul Michael, "Heat shock proteins and cell proliferation," *FEBS* 280:1–4 (1991).

Pelham, H.R.B., "Speculations on the Functions of the Major Heat Shock and Glucose–regulated Proteins," *Cell* 46, 959–61 (1986).

Pelham, "Heat shock and the sorting of luminal ER proteins" *EMBO J.* 8:3171–3176 (1989).

Redmond, Timothy, et al., "Immunofluorescence colocalization of the 90–kDa heat–shock protein and microtubules in interphase and mitotic mammalian cells," *Eur. J. of Cell Biol.* 50:66–75 (1989).

Rose, David W., et al., "Possible Involvement of the 90–kDa Heat Shock Protein in the Regulation of Protein Synthesis," *J. Biol. Chem.* 264:6239–6244 (1989).

Schlesinger "Heat shock proteins" *J. Biol. Chem.* 265:12111–12114 (1990).

Schlesinger, *Heat Shock: from bacterial to man* (Cold Spring Harbor, Cold Spring Harbor, NY 1982).

Seachrist, Lisa, "Ubiquitous Heat Shock Proteins Deal with Stress, Cancer," *J. of Nat. Cancer Institute* 85:1551–1552 (1993).

Sharp, Frank R., et al., "HSP70 Heat Shock Gene Regulation During Ischemia," *Stroke* Supp. I, 24(12):I72–I75 (1993).

Slepian, Marvin J., "Polymeric Endoluminal Paving" *Cardiology Clinics* 12(14):715–737 (1994).

Slepian, et al., "Pre–Conditioning Of Smooth Muscle Cells Via Induction Of Heat Shock Proteins Limits Proliferation Following Mechanical Injury", *67th Scientific Sessions Of The American Heart Assoc., & Circulation*, 90(4):1507 (1994) Abstract.

Sorger, Peter K., "Heat Shock Factor and the Heat Shock Response," *Cell* 65:363–366 (1991).

Trautinger, Franz, et al., "72–kD Heat Shock Protein Is A Mediator Of Resistance To Ultraviolet B Light", *J. Invest. Dermatol.*, 105(2):160–162 (1995) Abstract.

Walter, Michael, "The Induction Of Phenylpropanoid Biosynthetic Enzymes By Ultraviolet Light Or Fungal Elicitor By A Heat–Shock Treatment", *Planta,* 177(1):1–8 (1989) Abstract.

Welch, William J., "Mammalian Stress Response: Cell Physiology, Structure/Function of Stress Proteins, and Implications for Medicine and Disease," *Physiol. Reviews* 72:1063–1081 (1992).

Wilcox, et al., "Thrombotic Mechanisms In Atheroscleoris: Potential Impact Od Soy Proteins", *Journal Of Nutrition,* 125(3 Supp):631–638 (1995) Abstract.

Yellon, Derek M., et al., "Stress proteins—an endogenous route to myocardial protection: fact or fiction?" *Cardio. Res.* 27:158–161 (1993).

Zhang, Hua and Alice Y–C Liu, "Tributyltin Is a Potent Inducer of the Heat Shock Response in Human Diploid Fibroblasts," *J. Cell. Physiol.* 153:460–66 (1992).

StressGen Biotechnologies Corp. catalogue, "Does Your System of Study Involve Stress Proteins," (1995).

6h Pretreatment with hsp70 or hsp90 prior to scrape injury.

|  | % migration |
|---|---|
| Control | 100 ± 6 |
| hsp 70 | 125 ± 15 |
| hsp 90 | 87 ± 7 |

…

TREATMENT OF TISSUES TO REDUCE SUBSEQUENT RESPONSE TO INJURY

This application is a divisional of U.S. Ser. No. 08/321,128, filed Oct. 11, 1994 now U.S. Pat. No. 5,914,345 by Marvin J. Slepian and Stephen P. Massia entitled TREATMENT OF TISSUES TO REDUCE SUBSEQUENT RESPONSE TO INJURY.

BACKGROUND OF THE INVENTION

This invention relates to compositions and methods for pretreatment of tissue to modify the subsequent cellular response to injury, in particular, treatment of smooth muscle cells and other cells to reduce undesirable proliferation following injury.

Currently, many surgical and percutaneous therapies have been developed to (1) reopen blocked channels, conduits, and other critical lumens, (2) to remove undesirable diseased tissue, and (3) to implant substitute tissue, substitute tissue components, and deliver drugs. While these therapies are effective from a macroscopic perspective, from a cellular perspective, this interventional therapy simultaneously injures cells or cellular components of the manipulated tissues.

Specifically, therapeutic interventions, and especially surgical interventions, can cause unwanted subsequent responses by injured tissue. These can cause complications which can undo the effect of the intervention, or create new problems. For example, PCTA (percutaneous transluminal angioplasty) can recanalize and open stenotic or obstructed atherosclerotic arteries, but the incidental balloon mediated stretch and crush injury to the arterial wall can lead to proliferation of the smooth muscle cells of the media of the artery, resulting in reclosure of the artery ("restenosis") over the following months. This is observed in at least one-third of arteries treated. Another example is in the formation of adhesions after surgery, in which a chain of post-operative events leads to the formation or proliferation of adventitious tissue which binds internal body surfaces together, causing discomfort, organ malfunction and potential morbidity and mortality. This can occur in many tissues and organs, including the large and small intestine, the peritoneum, the heart, the pericardium, lungs, pleura, tendons, spinal discs, and paranasal sinuses.

Various interventions have been proposed to minimize such problems. These include the use of stents and coatings in arteries, for example, as reviewed by Slepian, in "Polymeric Endoluminal Paving" *Cardiology Clinics* 12(14) (November 1994) and Slepian, et al., *Circulation* 88(4):part 2, I-319 (1993), and as described by Hill-West, et al., *Proc. Natl. Acad. Sci. USA* 91:5967 (1994). In addition, the use of coatings, gels and fabrics may be utilized to prevent abdominal and pelvic adhesions as described by Hill-West, et al., *Obst. Gyne.* 83:59 (1994). These treatments have varying efficacy, and remain largely experimental.

These treatments are all administered after the injury has occurred, whether balloon angioplasty or surgery or other procedure, allowing the injured cells to initiate the complex cascade processes involved in clotting, complement activation, and cellular response to release of cytokines, inducers of proliferation, and other biologically active molecules. It is very difficult to stop these complex, interrelated processes once they have begun. The treatments described above serve merely to physically intercede between the injured cells and the surrounding tissue and blood, in an effort to minimize the reaction of the cells to these processes.

It is clearly desirable to develop methods and compositions to a priori minimize the reaction of cells and tissues, and of cells nearby or adjacent to them, to a subsequent injury. It is especially desirable to develop methods which are part of the body's normal response to injury and therefore multi-factorial in their response and limited in time, requiring minimal administration of exogenous or foreign material to the patient.

It is therefore an object of the present invention to provide methods and compositions for administration to patients to minimize subsequent cellular response to injury.

It is a further object of the present invention to provide compositions having limited term effect on cells which limits for a defined period of time their ability to overreact to injury.

SUMMARY OF THE INVENTION

An exogenous stimulus is applied to tissues or cells, which are at risk of injury in a subsequent surgical procedure or other intervention, which induces a response by the cells that minimizes reaction to the subsequent procedure. Stimuli can be chemical, physiological or physical. Examples include those stimuli known to induce expression of mammalian stress response proteins or heat shock proteins, especially heat shock protein 70 (hsp 70) and hsp 90, for example, exposure to heat or dilute hydrogen peroxide, or direct administration of exogenous heat shock proteins or stress response proteins, or those stimuli which act to inhibit or reduce stress response proteins or heat shock protein expression, for example, treatment with flavenoids. An amount effective to modulate stress or reduce the endogenous response is administered, based on in vitro assays which are used to determine levels of heat shock proteins or other stress response proteins or which are experimentally determined to reduce cell proliferation, thrombi formation, and matrix deposition following subsequent exposure to a procedure. Procedures include surgery, angioplasty, or abrasion. The method and compositions are also useful in mediating some disease processes, where the process involves undesirable migration.

In the preferred embodiment, the compositions which modulate the stress response in the targeted cells are locally administered to the area to be treated, although in some cases they may be administered systemically. Typically, local administration is achieved through the use of conventional devices such as catheters, laparoscopes, endoscopes, cannulae, means for injection such as syringes, or direct application. The stimuli may be heat, light, sound, irradiation or pressure, which are applied using standard means. Chemical stimuli can be applied in solution or in a delivery devices such as a polymeric film, stent, microparticles, or gel.

DETAILED DESCRIPTION OF THE INVENTION

Figure 1:
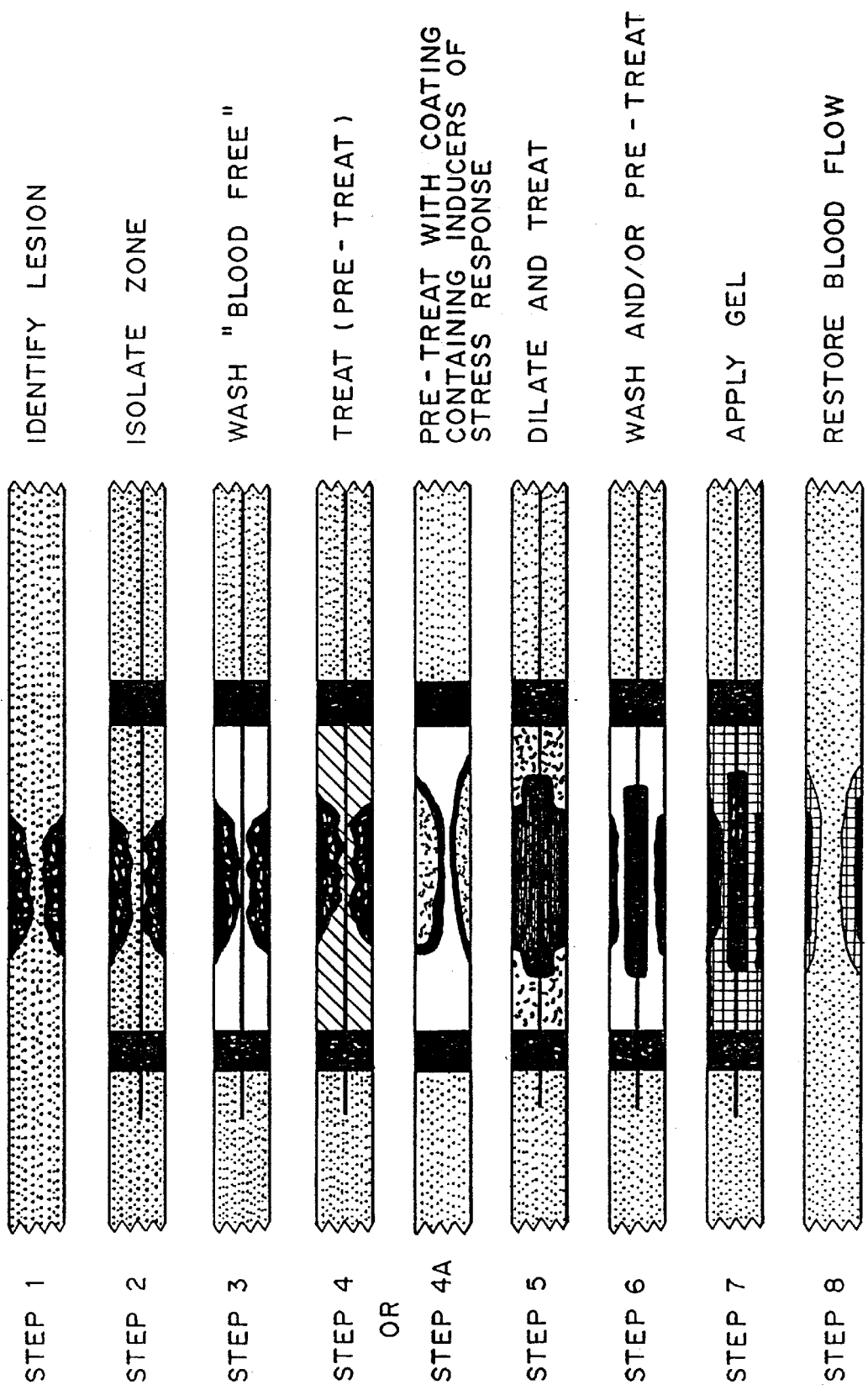
FIG. 1 is a schematic of a method by which a stimuli can be locally applied to the interior of a blood vessel to reduce the response to subsequent injury: step 1, identify lesion; step 2, isolate zone; step 3, wash "blood free"; step 4, treat (pre-treat); step 4*a*, "pre-treatment coating" containing inducers of stress response; step 5, dilate and treat; step 6, wash and/or pretreat; step 7, apply gel; and step 8, restore blood flow.

A therapeutic method has been developed to limit the response of tissues to a variety of injuries or disease states, by administration to the tissues of a physical or chemical treatment that alters the level of stress response proteins in cells of the tissue prior to injury or further disease development. The tissue can be further treated with the stimuli following injury or during the disease, in order to maintain altered levels of stress response proteins.

As used herein, altered levels of mammalian stress proteins and heat shock proteins can refer to elevated or reduced levels. Unless specifically stated otherwise, a reduction in proliferation of smooth muscle cells is generally induced by stimuli which can elevate levels of heat shock proteins such as hsp 90; a reduction in migration of transformed cells is generally induced by stimuli which can decrease levels of heat shock proteins such as hsp 27 or hsp 70.

As used herein, stimuli which alter the levels of heat shock proteins are exogenous stimuli, specifically, physical and/or chemical means which are administered to cells that result in an alteration of the levels of heat shock proteins expressed in the treated cells.

As used herein, procedures are treatments or other externally applied traumas imposed on tissues of a patient that can lead to undesirable proliferation of tissues, thrombi formation or matrix degradation. These can be surgical, percutaneous, macroscopic or microscopic.

As used herein, disease processes are those which involve undesirable migration of cells and for which a correlation with expression of heat shock proteins has been demonstrated.

Stimuli of Heat Shock Proteins

As used herein, both physical and chemical stimuli can be used to induce expression of heat shock proteins. The most frequently studied stimuli are heat, oxidants, and heavy metals. Alternatively, or in addition, heat shock proteins can be directly administered to the cells to be treated. Those that are believed to correlate with a response to injury include hsp70, hsp 90 and other cytoplasmic heat shock proteins. Assays to measure the levels of these proteins are well known to those skilled in the art. However, it should be noted that the inducement of heat shock proteins may not be the actual mechanism by which a beneficial effect is obtained, but merely an indicator that appropriate conditions have been used which result in the desired beneficial effect.

Several reviews of heat shock proteins have been published, the teachings of which are incorporated herein, including Schlesinger, *Heat Shock:from bacterial to man* (Cold Spring Harbor, Cold Spring Harbor, N.Y. 1982); Lindquist, "The heat-shock response" *Ann. Rev. Biochem.* 55:1151–1191 (1986); Pelham, H. R. B., "Speculations on the Functions of the Major Heat Shock and Glucose-regulated Proteins," *Cell* 46, 959–61 (1986); Lindquist and Craig, "The heat-shock proteins" *Annu. Rev. Genet.* 22:631–677 (1988); Pelham, "Heat shock and the sorting of luminal ER proteins" *EMBO J.* 8:3171–3176 (1989); Schlesinger "Heat shock proteins" *J. Biol. Chem.* 265:12111–12114 (1990); Kaufmann, "Heat shock proteins and the immune response" *Immunol. Today* 11:129–137 (1990); Morimoto "Heat shock: the role of transient inducible responses in cell damage, transformation, and differentiation" *Cancer Cells* 3:295–301 (1991); Nover, "HSFs and HSPs—a stressful program on transcription factors and chaperones." *Stress Proteins. and the Heat Shock Response,* sponsored by Cold Spring Harbor Laboratory (Cold Spring Harbor, N.Y. USA April 29–May 2, 1991) *Nature New Biol.* 3:855–859 (1991); and Nover and Scherf "Heat shock protein, in *Heat Shock Response* (CRC Press, 1991) pp. 41–127. As demonstrated by "Requirement for hsp70 in the mitochondrial matrix for translocation and folding of precursor proteins" Kang, et al., *Nature* 348, 137–143 (November 1990); and "Mitochondrial proteins essential for viability mediate protein import into yeast mitochondria" Baker and Schatz, *Nature* 349, 205–208 (January 1991), the Hsp70 proteins are found primarily in the nucleus/nucleolus, cytoplasm, and lumen of the endoplasmic reticulum; function primarily in the nucleus, nucleolus, and cytoplasm in binding unfolded proteins resulting from stress and unfolding proteins before their translocation into mitochondria and the endoplasmic reticulum (Deshaies, R. J., et al., "A subfamily of stress proteins facilitates translocation of secretory and mitochondrial precursor polypeptides," *Nature* 332, 800–805 (1988).

Physical Inducers

Exposure of cells to heat over a temperature range of about 40 to 60° C., preferably 41 to 50° C., most preferably 42 to 45° C., for a period of at least one minute and up to an hour, induces heat shock. For example, heating of cells to 42° C. for a period of a few minutes to an hour induces high levels of heat shock proteins.

Heat is typically applied by direct contact of the cells with a source of heat, for example, a solution or a device such as a catheter containing a thermocouple, where the heat is applied directly or via a reservoir such as a polymer or gel, to the cells. In some cases, localized heating may be achieved using a laser, infrared, or microwave. The conditions should be sufficient, in the cells to be stimulated, to produce a temperature of at least about 42° C. for at least about one minute and which do not kill the cells. Where the cells are close to the skin, heating may be achieved by application of a heating pad. Of the physical methods of induction of the response which could be used, locally applied, gentle heating is preferred. Heating can also be indirect, by heating blood or other fluid permeating the organ or tissue.

Whole body hyperthermia can also be used to used induce heat shock proteins, for example, as described by Black and Luchesi, *Circulation* 83(3), 1048–51 (1993), and Currie et. al., *Circulation* 83(3), 965–971 (1993) who demonstrated that whole-body hyperthermia induces a transient resistance to the effects of ischemia and reperfusion in rabbit hearts.

Whole body heating is acceptable in small animals or microorganisms, but is less preferred for humans.

Cold, ischemia and anoxia can also be used. to induce expression of stress proteins or heat shock proteins. Ultrasound may also induce stress proteins or heat shock proteins. Radiation at frequencies other than those which generate heat can also be used to induce stress proteins.

Chemical Inducers

A number of chemicals which are relatively safe and non-cytotoxic, can be administered to cells to induce expression of heat shock proteins. For example, hydrogen peroxide, at a concentration of 1 mM, has been found to be effective without systemic effects.

Many treatments are described in the literature which can induce the production of HSP or stress proteins (SP) by cells. These include heat shock and anoxia or ischemia as described above; hydrogen peroxide and ethanol (Courgeon, et al., *Exp. Cell Res.* 204:30–37, 1993); herbimycin A, an antibiotic (Murakami et al, *Exp. Cell Res.* 195:388–344, 1991); transition metals (such as copper, zinc, mercury and cadmium) and sulfhydryl-oxidizing or binding agents (such as arsenite) (Levinson, et al., *Biochim. Biophys. Acta* 606:170–80, 1980); tributyltin (Zhang and Liu, *J. Cell. Physiol.* 153:460–66, 1992).

Repressors

Conditions are also known which repress the induction of the heat shock response. These include the addition of flavonoids, such as quercitin, as described by Hosokawa, et al., in Cell Structure and Function; *Jap. Soc. Cell Biol.* 393–401 (1990). Hosokawa, et al., discloses the use of flavone, flavonol, isoflavone, luteolin, quercetin, genistein, and kaempferol, in the range of 25 to 300 $\mu$M, as inducers or repressors of hsp 70, hsp 110, and hsp 40. The flavone and the flavenols quercetin and kaempferol inhibit the induction of hsp by heat; luteolin and rutin at these dosages had little effect on hsp induction.

Direct Administration of HSP

Heat shock proteins are available in purified form from Stress Gen, British Columbia, Canada. These are administered in a dosage equivalent to between 1 pM to 100 mM, with a preferred range of 1 to 100 $\mu$M, most preferably 10 $\mu$M, in a suitable pharmaceutically acceptable carrier.

Enhancers of penetration such as detergents, for example, sodium deoxycholate, or liposomes, can be used to enhance delivery, as can physical enhancers such as vibration and ultrasound. Conjugates or particles can also be used to enhance cellular uptake by phagocytosis, pinocytosis or viropexis.

Administration of Inducers or Repressors

In addition to administration before the injury or insult, administration of inducing agents may be conducted during a procedure, and optionally continued for a short time after the procedure, to ensure the passivation of the tissue. Moreover, the administration of the inducing stimulus could occur over a prolonged time before the application of the injury stimulus.

Carriers for Administration

Administration of inducers may be either systemic, or localized to the affected site or region. Administration may be by any appropriate means, as indicated above, including ingestion, transmucosal delivery, transdermal delivery, implantable devices, microspheres, gels, porous polymeric materials, microcapsules, drug-delivery catheters such as those described in U.S. Pat. Nos. 5,328,471 and 5,213,580, indwelling catheters, or drip infusions.

Polymeric materials that are useful for delivery of the stimulus include non-biodegradable and biodegradable, biocompatible polymers. Representative synthetic polymers are polyamides, polycarbonates, polyalkylenes and polyalkylene glycols or oxides, polyvinyl alcohols, ethers or esters, polymers of acrylic and methacrylic esters, polyethylene, polypropylene, poly(ethylene glycol), ethylene vinyl acetate, polymers of lactic acid and glycolic acid, polyanhydrides, poly(ortho)esters, polyurethanes, poly (butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, the biodegradable materials degrade either by enzymatic hydrolysis or exposure to water in vivo, by surface or bulk erosion.

Application of the Stimuli

1. Administration of Stimuli to Tissue Lumens

The stimulus is preferably applied using a single catheter with single or multiple balloons and lumens. The catheter should be of relatively low cross-sectional area. A long thin tubular catheter manipulated using fluoroscopic guidance is preferred for providing access to the interior of organ or vascular areas. In the preferred embodiment, a stimuli can be delivered to a desired location within a lumen by introducing a catheter into the tissue lumen, wherein the catheter has two expansile members, typically balloons, and means for supplying the stimuli at a space between the two members; expanding the expansile members to occlude the targeted portion of the lumen, administering the stimuli, contracting the expansile members, and removing the catheter. In one preferred embodiment, the catheter is also used to wash out the occluded region so that, in the case of a blood vessel, the region is substantially free of blood. However, the stimulus may also take the form of a heating element which is used to heat the blood within the region to be treated.

The tissues involved may be those organs or structures having hollow or tubular geometry. Alternatively, the tissue may be a normally solid organ in which a cavity has been created either as a result of a surgical procedure, a percutaneous intervention, an accidental trauma, or disease. Examples of hollow vessels include the aorta, coronary arteries, veins and lymphatic vessels. Examples of hollow organs include the heart, the eye, intestine, fallopian tube, uterus, kidney or the bladder. In addition many organs have component structures which are hollow such as the trachea (lung), the biliary duct (gall bladder), or the pancreatic duct (pancreas). Moreover, many solid organs possess internal "true" spaces, such as cavities, cavernous sinuses or lumens, or "potential" spaces, following a disease process which creates the space, i.e., the interior of a necrotic tumor.

2. Administration of Polymeric Material to Tissue Surfaces

In another embodiment, the stimulus is applied in or with a polymeric material which is positioned in contact with or in the vicinity of a tissue or cellular surface to be treated. The polymeric material is applied using a catheter, syringe, or spray, depending on the tissue lumen surface to which it is applied. Such devices are known to those skilled in the art, such as a modified PTCA catheter of the type described above.

Once the polymeric material has been applied, the material may be reconfigured to form a coating or "paving" layer in intimate and conforming contact with the surface. The resulting paving layer can have a sealing function, i.e., it forms a coating of sufficiently low porosity that it excludes macromolecules (i.e., less than 53 Angstroms for a small protein up to 2000 Angstroms for a rod such as myosin) and cells (600 nm for platelets up to 30 to 40 microns for large cells). The coating preferably has a thickness on the tissue surface on the order of 0.001–1.0 mm, however, coatings having a thickness outside this range may be used as well. By appropriate selection of the material employed, using materials commercially available, and methods for crosslinking that are known to yield a specific percent crosslinking and porosity, and of the configuration of the paving material, the process can be tailored to satisfy a wide variety of biological or clinical situations.

The polymeric materials may be applied in custom designs, with varying thicknesses, lengths, and three-dimensional geometries (e.g. spot, stellate, linear, cylindrical, arcuate, spiral) to achieve varying finished geometries. Further, the process may be used to apply material to the surfaces of any biological tissue, especially hollow, cavernous, or tubular biological structures (whether natural or artificially formed) in either single or multi-layer configurations. The process may also be used, where appropriate, to occlude a tissue lumen completely.

In some cases, the polymeric material is polymerized in situ. In this case, the means for polymerizing the polymer may itself serve as the stimulus. In other cases, the stimulus may be applied in the polymeric material, where it diffuses into the surrounding tissue, or supplied into the lumen so that it diffuses through the polymeric material at a controlled rate to the underlying tissue.

FIG. 1 is a schematic of the process for applying polymeric material to a tissue lumen. In step 1, a lesion in the lumen is identified and isolated. In step 2, a catheter, optionally a balloon catheter consisting of a tubular shaft which includes one or more balloons, is inserted into the lumen. In the preferred embodiment for the treatment of blood vessels, the-distal occlusion balloon is used to occlude the distal end of a treatment site. In embodiments where the lumen can be rinsed clean, for example at an end artery or in the gastrointestinal tract or lungs, it is not necessary to inflate the balloon. In any case, the treatment site is cleared of blood, mucous, or other extraneous material, as shown in step 3. The site may then be treated with drugs, for example a drug inhibiting responsiveness to mechanical stimuli or cell proliferation, as shown in step 4. In step 5, if appropriate, the lesion itself is treated by expansion of the balloon, in the case of an arterial plaque, or by other mechanical, thermal, optical, photochemical, ultrasonic, or radiation means. As shown in step 6, the site is again treated with drugs and/or washed or compounds to increase adhesiveness applied. optionally, in step 7, the polymeric material is applied in combination with the stimuli and polymerized, solidified or configured. The stimuli can itself be the means for polymerization of the polymeric material.

Step 4a is an optional step in which stress induction is either short term, sub-acute or chronic. In a short term induction, steps 1, 2, 3, are performed, step 4 where induction is performed for between one minute and one hour, then steps 5, 6, 7 and 8 are performed. In a subacute induction, steps 1, 2, and 3 are performed, step 4 is performed over a period of an extended time, such as overnight, where a zone is occluded and a bypass is performed, for example, using a continuous catheter, or by implantation of a controlled release device such as a polymeric gel, then steps 5, 6, 7 and 8 are performed. In chronic induction, steps 1, 2, 3, 4, and 4a are performed, using a gel, pavent, or ectoluminal sleeve, as described in more detail below, in combination with operative or percutaneous therapies, followed by steps 5, 6, 7, and 8.

In some embodiments the catheter includes a "mold core" which is used to shape the polymeric material so that it covers only the area to be treated in a thin layer. The central mold core member may be able to adjust size, i.e., for a balloon it may be underinflated to not occupy the maximum space, thereby leaving room for the polymeric material. The polymeric material may be shaped as a uniform layer, or patterned or segmented as desired. In step 8, the catheter is removed and flow of material through the lumen is restored.

Figure 2:
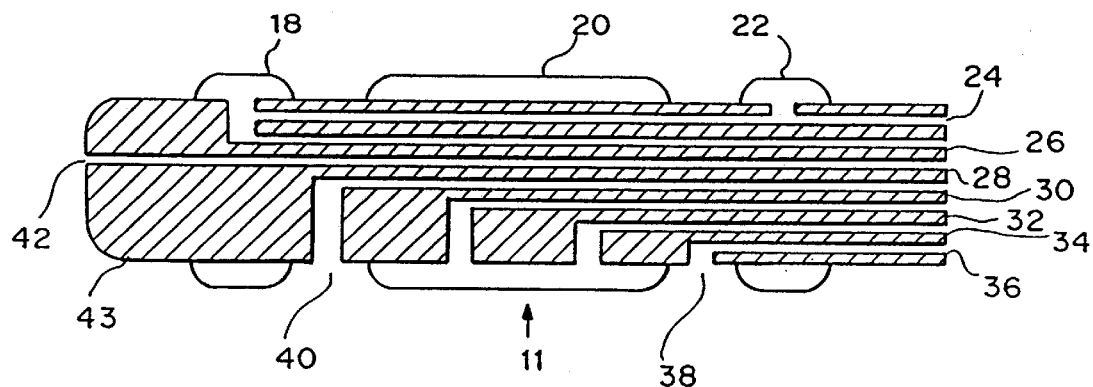
FIG. 2 is a perspective drawing of a single catheter with means for entering a tissue lumen, isolating a zone, washing, applying a drug, adhesive-and/or a polymeric material and a core forming member and/or dilating member.
Figure 3:
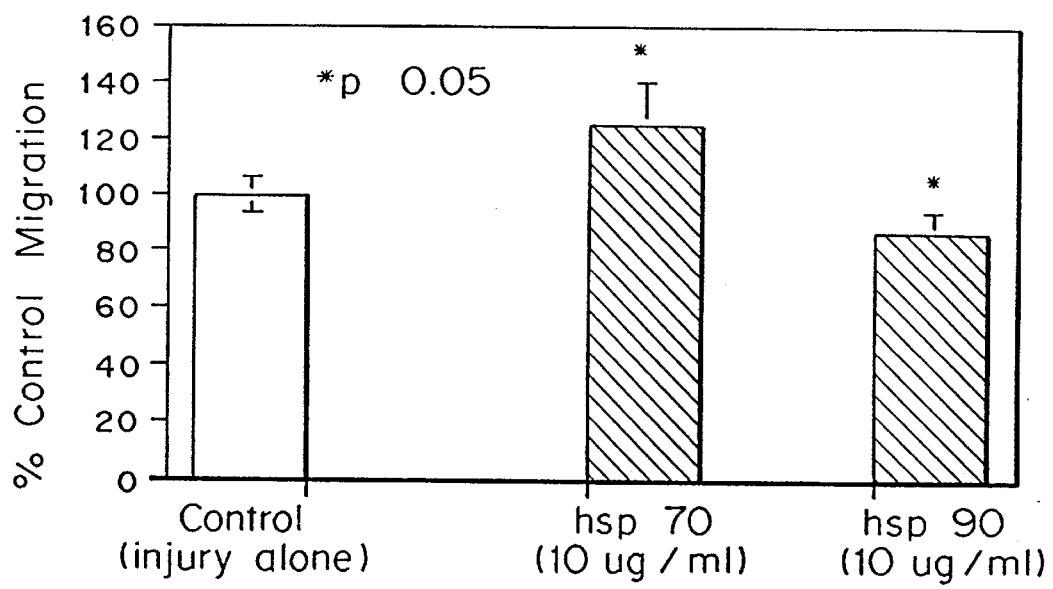
FIG. 3 is a graph of percent control migration for control (injury alone), hsp 70 (10 µg/ml), and hsp 90 (10 µg/ml), to demonstrate the effect of heat shock protein pretreatment on post-injury SMC migration.

Two other embodiments of delivery catheters that can be utilized for application of the polymeric material are shown in FIG. 2. FIG. 2 is a single catheter with means for entering a tissue lumen, isolating a zone, washing, applying a drug, adhesive and/or a polymeric material and a core forming member and/or dilating member. The catheter 11 is constructed with two isolation balloons 10, 14, and a central dilating or molding balloon 12, as well as a plurality of lumens and an attached reservoir 16 for delivering washing fluid, drug, adhesive and/or polymer. Two isolation balloons 18, 22 are constructed out of elastomeric material, i.e., latex, krayton or C-flex or thermoplastic polymers such as polyethylene, polyolefin co-polymer, polyethylene terepthalate, or nylon. The balloons 18, 22 are attached to a multi-lumen shaft 43 including a central lumen 42 running the length of the device to allow flushing or passage over a guide wire (not shown). A central mold-core balloon 20 is fabricated out of similar materials to those forming the isolation balloons 18, 22, or from less compliant materials so that it opens to a designated dimensions without a continuous stretch or expansion via creep of the balloon material. In addition, lumens exist for filling the isolation balloon 24, 26 and for instilling, filling or removing fluid from the dilating or mold core balloons 32, 34. In addition, there are lumens 30, 36 for instilling fluid into the isolation zone. Lumens 38, 40 are used to instill fluid or remove fluid from the isolation zone. This device provides a means to instill, perfuse, or superfuse a zone.

Catheter bodies are made of standard materials, including metals such as surgical steel and thermoplastic polymers. Occluding balloons may be made from compliant materials such as latex or silicone, or non-compliant materials such as polyethylene terephthalate (PET). The expansible member is preferably made from non-compliant materials such as PET, (PVC), polyethylene or nylon. If used, the balloon catheter portion of a dilatation may optionally be coated with materials such as silicones, polytetrafluoroethylene (PTFE), hydrophilic materials like hydrated hydrogels and other lubricous materials to aid in separation of the polymer coating.

3. Other Means for Application

The stimulus and/or polymeric material may also be applied to the surface to be coated by spraying, extruding or otherwise delivering the material via a delivery device having single or multiple lumens. Application of the stimulus and/or polymer material may be accomplished by extruding a solution, dispersion, or suspension of monomers, polymers, macromers, or combinations thereof through a device to coat or fill a tissue or cellular surface, a tissue lumen or a hollow space. The formation of the coating can be controlled by introducing crosslinking agents, gelling agents or crosslinking catalysts together with the fluent material and then altering the conditions such that crosslinking and/or gelling occurs. Thus, when a balloon catheter is used, a flow of heated or chilled fluid into the balloon can alter the local temperature to a level at which gelling or cross-linking of introduced material is induced, thereby rendering the material non-fluent and also serving as the stimulus for inducement of heat shock proteins. Localized heating or cooling can be enhanced by providing a flow of heated or chilled liquid directly onto the treatment site. Thermal control can also be provided, however, using a fluid flow through or into the balloon, or using a partially perforated balloon such that temperature control fluid passes through the balloon into the lumen. Thermal control can also be provided using electrical resistance heating via a wire running along the length of the catheter body in contact with resistive heating elements. This type of heating element can make use of DC or radio frequency (RF) current or external RF or microwave radiation. Other methods of achieving temperature control can also be used, including light-induced heating using an internal optical fiber (naked or lensed). Similar devices can be used for application of light, ultrasound, or irradiation.

Medical Indications for Treatment

1. Treatment of Lumen Surfaces

In addition to treatment of arteries, the method described herein can be utilized for other applications such as treating the interior of veins, ureters, urethras, bronchi, biliary and pancreatic duct systems, the gut, nasolacrimal ducts, sinus cavities, the eye, and eustachian, spermatic and fallopian tubes. The process can be used for treatment in the context of transjugular intrahepatic portosystemic shunting procedure (TIPS), dialysis grafts, arterio-venous fistulae, and aortic and other arterial aneurysms, as well as in the treatment of abrupt vessel reclosure post PCTA, the treatment of significant vessel dissection, the treatment of vessel wall "flaps" either secondary to catheter injury or spontaneously occurring, and the treatment of aneurysmal coronary dilations associated with various arteritidies.

The hollow or cavernous geometry present in many body components has functional significance. Such geometry facilitates fluid (blood, urine, lymph, bile) gas, a cellular (ovary, spleen) containment or transport. These hollow vessels, organs and organ components are typically composed of several tissue layers. Generically these organs are composed of an inner cellular layer typically functioning as a barrier layer, one or several middle functional layers containing muscularis, glands or other functional tissue, and an external supportive or stromal covering layer.

Disease may effect the innermost layer of these hollow organs and thereby violate their barrier function. Diseases can be either: (1) systemic with overall diffuse constitutional manifestations, (2) systemic with localized specific intra-organ focal involvement, or (3) localized only with definitive regional intra-organ involvement. Examples of such diseases include spontaneous plaque rupture, unstable angina, non-cardiogenic pulmonary edema, sepsis, and erosive/infiltrative tumors.

The following are examples of typical ways in which the methods and materials described herein can be applied in clinical practice.

2. Preconditioning of an Arterial Zone Prior to Angioplasty

A patient is brought to the catherization laboratory and a coronary guide catheter is placed into the coronary ostia and a multi-balloon drug administration catheter is placed into the coronary artery and advanced to the desired location at the site or adjacent to the lesion to be treated. The stimulus, i.e., the inducing agent in flowable form, is then infused, perfused or superfused at the site in the correct dose for the appropriate length of time. The typical time of the administration may be anywhere from seconds to hours, with an average of 10 to 15 minutes. Following delivery of the stimulus, the delivery catheter is removed and an angioplasty balloon catheter will then be placed in the zone and an angioplasty performed.

While the above is a general outline of administration of the stimulus immediately prior to angioplasty, the method may be varied as follows. The stimulus may be administered by a variety of drug delivery catheters including balloons with holes such as that described to U.S. Pat. Nos. 5,087,244 and 4,636,195 to Wolinsky; or other suitable catheters such as those described by U.S. Pat. No. 5,092,841 to Spears, U.S. Pat. No. 550,238 to Allen, U.S. Pat. No. 5,295,962 to Crocker, et al., U.S. Pat. Nos. 3,173,418, 4,423,725 or 4,417,570 to Baran, U.S. Pat. No. 4,445,892 to Hussein, et al., U.S. Pat. No. 5,306,250 to March, U.S. Pat. No. 5,279,565 to Klein, WO89/12478 by Just, and DE3833359A1 by Bockenagian. Channelled or electroporation catheters can also be used, for example, as described by U.S. Pat. No. 5,306,249 to Don Michael. For isolating a zone using an endoscope, one could use the endoscope described by U.S. Pat. No. 4,224,929 to Furihata. U.S. Pat. No. 4,693,720 to Scharnberg discloses a material for application of materials to the skin. The stimuli may be administered in a solution, slurry, gel, emulsion, particles or in any other combination thereof. In addition to using a straight solvent, a mild detergent or permeation enhancer may be co-mixed with the stimuli.

This method of administration may be utilized not only in association with angioplasty but may also be utilized prior to atherectomy, laser angioplasty or stenting.

As opposed to when the stimulus is administered immediately prior to the intervention, in certain cases it may be best to deliver the stimulus which induces a stress response hours or days prior to the injurious therapy. For example, a patient may be admitted-to the hospital and brought on the next day to the catherization laboratory as described above, a similar guide catheter placed in the coronary artery and a drug delivery catheter placed at the site of the lesion, and the lesion bathed with the stimulus for minutes to hours. The device would then be removed with the agent working locally overnight inducing the stress response in the arterial wall tissue at the site of the lesion. The patient is then brought down the next day to the catherization laboratory for angioplasty, atherectomy or stenting. In this case, these injurious therapies would be effected on a tissue which was enriched with stress response proteins and hence would be more capable of handling the injurious therapy with a subsequently modified or abrogated response.

In addition to administration hours or days prior to therapy, in certain instances a continuous so infusion catheter could be utilized to administer the stimulus at the site of the lesion continuously up until the time of angioplasty. Therapy might also be continued during or after the angioplasty in certain cases.

3. Development of a Chronic Stress Response

In certain instances it might be best to chronically induce a stress response to ensure complete enrichment of the tissue with stress proteins and development of a chronic stress state to alter the physiology of the tissue prior to injury. In this type of setting as relates to angioplasty, a patient may be brought in and the lesion treated using catheter systems and approaches as outlined above, however, the patient may receive multiple, weekly, or a single application of the stimulus in a sustained release or a controlled release polymeric implant such as outlined above using either a solid polymer or gel, particles or other sustained release vehicles. Several weeks to months later, the patient can be brought in for the therapeutic injury, e.g, angioplasty.

4. Application of Stimulus in a Surgical Setting

During colonic surgery, following exposure of the bowel, appropriate stimuli can be directly applied to the intestinal serosal surface. Alternatively, the inducers can be applied as a slurry within the peritoneum prior to making of any incisions in the colon. Direct colonic incisions are then performed following this pre-treatment with the stimulus. Subsequent colonic re-anastomosis at the completion of surgery would then occur with tissue enriched with stress response proteins. In addition, inducers may be applied within the intestine or at the anastomotic site via an external polymeric gel, within soaked sutures or in pledgets.

This type of therapy may also be delivered laproscopically.

The present invention will be further understood by reference to the following non-limiting examples.

EXAMPLE 1

Use of an Inducing Stimulus to Prevent Cell Proliferation in Vitro

A study was conducted to determine the effect of various agents known to be activators of the heat shock response on tissue. Confluent cultures of rat aortic smooth muscle cells (third passage) were pretreated with the following known inducers of HSP: tributyl tin, 0.6 $\mu$M, 6 hrs; $CdCl_2$, 10 $\mu$M, 6 hrs; heat, 42° C., 2 hrs; and $H_2O_2$ (hydrogen peroxide), 1 mM, 1 min. Cells treated with medium alone (DMEM+10% FCS) were used as uninduced controls. Cultures were then wounded by a scrape injury, washed in fresh medium, and incubated in medium without the HSP inducer.

It was confirmed by immunohistochemistry that all inducing treatments induced expression of the proteins HSP70 and HSP90, using antibodies obtained from StressGen, and standard immunohistochemistry techniques. At 24 hours, cell proliferation was assessed by determination of incorporation of tritiated deoxythymidine (TdT), and migration was assessed by measurement of mean distances of cells migration from the edge of the wound.

The results in Table I are reported as % and standard deviation of TdT and of migration compared to uninduced controls. Statistical significance is denoted: *,p<0.01; +, p<0.05

TABLE I

Effect of HSP Inducers on Cells.

| Treatment | % TdT Incorporation | % Migration |
|---|---|---|
| 42° C. | 16.1 ± 2.6* | 94.0 ± 4.0+ |
| Tributyltin | 28.2 ± 2.2* | 135.0 ± 10.0 |
| Cadmium dichloride | 9.0 ± 1.3* | 122.0 ± 2.6* |
| Hydrogen peroxide | 26.1 ± 1.9* | 138.0 ± 13.0° |

Thus, incubation of cells with all of these diverse treatments selectively inhibits their proliferation (as measured by TdT incorporation), while the chemical reagents, but not heat treatment, stimulate migrate. The unimpaired or enhanced mobility also implies that the stimulators lack severe toxicity.

EXAMPLE 2

Use of an Inducing Stimulus to Prevent Cell Proliferation in Vivo

The above experiment is replicated in denuded carotid arteries of rabbits. Rabbit arteries are damaged as described in Hill-West, et al. *Proc. Nat. Acad. Sci. USA* 91:5967–71 (1994). Rabbits are conventionally heparinized. Prior to the denudement, experimental arteries are exposed to 1 mM hydrogen peroxide in buffered isotonic saline for 1 minute, while no pretreatment is given to control arteries. Thickening of the arterial wall is evaluated at 14 days as described in Hill-West et al. Significant diminishment of medial thickening is observed in peroxide pretreated arteries.

EXAMPLE 3

Inducing Stimulus in the Presence of an Antithrombotic Gel Coating

The above study is repeated, except that after exposure to 1 mM peroxide and denudement, arteries are coated with gel as described in Hill-West et al. Heparinization is omitted. Results at 14 days show a statistically significant reduction in hyperplasia compared to controls for peroxide-treated arteries.

EXAMPLE 4

Pretreatment of SMCs with Exogenous HSPs Affect Injury-induced SMC Migration

The following study was used to demonstrate the effect of direct administration of hsp on smooth muscle cells (SMCs). Monolayers of SMCs in culture were treated with hsp 70 (10 $\mu$g/ml final concentration) or hsp 90 (10 $\mu$g/ml final concentration) obtained from Stress Gen, British Columbia for six hours pretreatment at 37° C.

Cell monolayers were then scraped as described above, media decanted, washed, replaced with fresh DMEM+10% FCS, and examined after 24 hrs for migration.

The results showed that the percent migration for pretreatment of cells with hsp 70 was 125±15 percent of control; with hsp 90 was 87±7 percent of control.

Modifications and variations will be obvious to those skilled in the art from the foregoing detailed description. Such modifications and variations are intended to be encompassed by the following claims.

We claim:

1. A composition for altering subsequent cellular responses to a therapeutic intervention at a tissue locus in vivo, the composition comprising a reagent or a material inducing a change in a physical condition, in a physiologically acceptable carrier or manner, in an amount effective to induce altered levels of heat shock proteins or stress response proteins in cells to be treated and thereby alter proliferation or migration of cells which would otherwise occur in response to a therapeutic intervention.

2. A method of making a composition suitable for altering subsequent cellular responses to a therapeutic intervention at a tissue locus in vivo, comprising mixing an agent known to act as an inducing stimulus on the targeted cells as determined by altered expression of heat shock proteins or stress response proteins, with a pharmaceutically acceptable carrier.

3. The method of claim 1 further comprising mixing the stimulus with an immobilizing system.

4. The composition of claim 1 wherein the reagent or physical condition is a physical stimulus selected from the group consisting of heat, cold, ultrasound, light, vibration, and pressure in an amount effective to induce expression of stress response proteins or heat shock proteins without killing the cells to be treated.

5. The composition of claim 1 wherein the reagent or physical condition is a physiological stimulus selected from the group consisting of glucose deprivation and oxygen deprivation.

6. The composition of claim 1 wherein the reagent or physical condition is a chemical stimulus selected from the group consisting of oxidants and heavy metals in an amount effective to induce expression of stress response proteins or heat shock proteins without killing the cells to be treated.

7. The composition of claim 1 wherein the reagent or physical condition is a flavonoid in an amount effective to reduce expression of heat shock proteins without killing the cells to be treated.

8. The composition of claim 1 wherein the treated cells exhibit decreased proliferation as compared with untreated cells following exposure to trauma.

9. The composition of claim 1 wherein the treated cells exhibit decreased migration as compared with untreated cells following exposure to the stimulus.

10. The composition of claim 1 further comprising a polymeric material.

11. The composition of claim 10 wherein the polymeric material is selected from the group consisting of hydrogels, organogels, polymeric films, and microparticles.

12. The composition of claim 1 wherein the reagent or physical condition is a purified stress response protein or heat shock protein.

13. The composition of claim 12 wherein the reagent or physical condition is a heat shock protein.

* * * * *